United States Patent [19]

Dolak et al.

[11] Patent Number: 4,689,300

[45] Date of Patent: Aug. 25, 1987

[54] ANTIBIOTIC PRODUCING STREPTOMYCES THIOLACTONUS

[75] Inventors: Lester A. Dolak, Plainwell; Alice L. Laborde, Kalamazoo; Oldrich K. Sebek, Kalamazoo; Thomas M. Castle, Kalamazoo; Thomas F. Brodasky, Kalamazoo, all of Mich.

[73] Assignee: The Upjohn Company, Kalamazoo, Mich.

[21] Appl. No.: 778,828

[22] Filed: Sep. 23, 1985

Related U.S. Application Data

[62] Division of Ser. No. 515,077, Jul. 18, 1983, Pat. No. 4,565,699.

[51] Int. Cl.$^4$ .................. C12N 1/20; C12P 13/02; C12R 1/465
[52] U.S. Cl. .................. 435/253; 435/129; 435/886
[58] Field of Search ............... 435/253, 129, 886, 118

[56] References Cited

PUBLICATIONS

Sasaki, H. et al.; 'Thiolactomycin, A New Antibiotic, II Structure Elucidation'; *J. Antibiotics*, vol. 35, No. 4, pp. 396–400; Apr. 1982.

Omura, S. et al.; 'Thiotetromycin, A New Antibiotic, Taxonomy, Production, Isolation and Physiochemical and Biological Properties'; *J. Antibiotics*, vol. 36, No. 2, pp. 109–114, Feb. 1983.

Shizuri, Y. et al.; 'Isolation and Structure of Citreothiolactone, a Novel Metabolite of *Penicillium Citreo-Viride B.*'; *Tetrahedron Letters*, vol. 24, No. 10, pp. 1053–1054; 1983.

*Primary Examiner*—Thomas G. Wiseman
*Assistant Examiner*—Elizabeth C. Weimar
*Attorney, Agent, or Firm*—Paul J. Koivuniemi

[57] ABSTRACT

Novel antibiotic U-68,204 is produced in a fermentation under controlled conditions using a biologically pure culture of the microorganism *Streptomyces thiolactonus*, NRRL 15439. This antibiotic is active against various Gram-positive bacteria. Thus, antibiotic U-68,204 can be used in various environments to eradicate or control such bacteria.

1 Claim, 4 Drawing Figures

ANTIBIOTIC PRODUCING *STREPTOMYCES THIOLACTONUS*

This is a divisional of application Ser. No. 515,077 filed July 18, 1983 now U.S. Pat. No. 4,565,699, issued Jan. 21, 1986.

BACKGROUND OF THE INVENTION

Antibiotic U-68,204, of the subject application, is related to thiolactomycin. See H. Sasaki, et al., J. Antibiotics, 35, 396 (1982). It also is related to citreothiolactone, but not as closely. See Y. Shizuri, et al., Tet. Letters, 24, 1053 (1983). Further, U-68,204 is related to thiotetromycin. See S. Omura, et al., J. Antibiotics, 36, 109 (1983). Antibiotic U-68,204 differs structurally from thiotetromycin in that one of the methyl groups of thiotetromycin is converted to an amide. The structural similarities are as shown in Chart I.

BRIEF SUMMARY OF THE INVENTION

Antibiotic U-68,204 is producible in a fermentation under controlled conditions by a biologically pure culture of the new microorganism *Streptomyces thiolactonus*, NRRL 15439.

Antibiotic U-68,204 is an acidic compound which is active against various Gram-positive bacteria. Thus, antibiotic U-68,204 can be used to disinfect washed and stacked food utensils contaminated with *S. aureus*. It can also be used as a disinfectant on various dental and medical equipment contaminated with *S. aureus*. Still further, antibiotic U-68,204 can be used as a bacteriostatic rinse for laundered clothes and for impregnating papers and fabrics; it is also useful for suppressing the growth of sensitive organisms in plate assays and other microbiological media.

DETAILED DESCRIPTION OF THE INVENTION

Chemical and Physical Properties of Antibiotic U-68,204

Molecular Weight: 267

Elemental Analysis: Found: C, 58.32; H, 6.68; N, 5.01; S, 10.91. Calc'd: C, 58.43; H, 6.37; N, 5.24; S, 11.99.

Color of Crystals: White

Molecular Formula: $C_{13}H_{17}NO_3S$

Melting Point: 98°–101°

Figure 1:
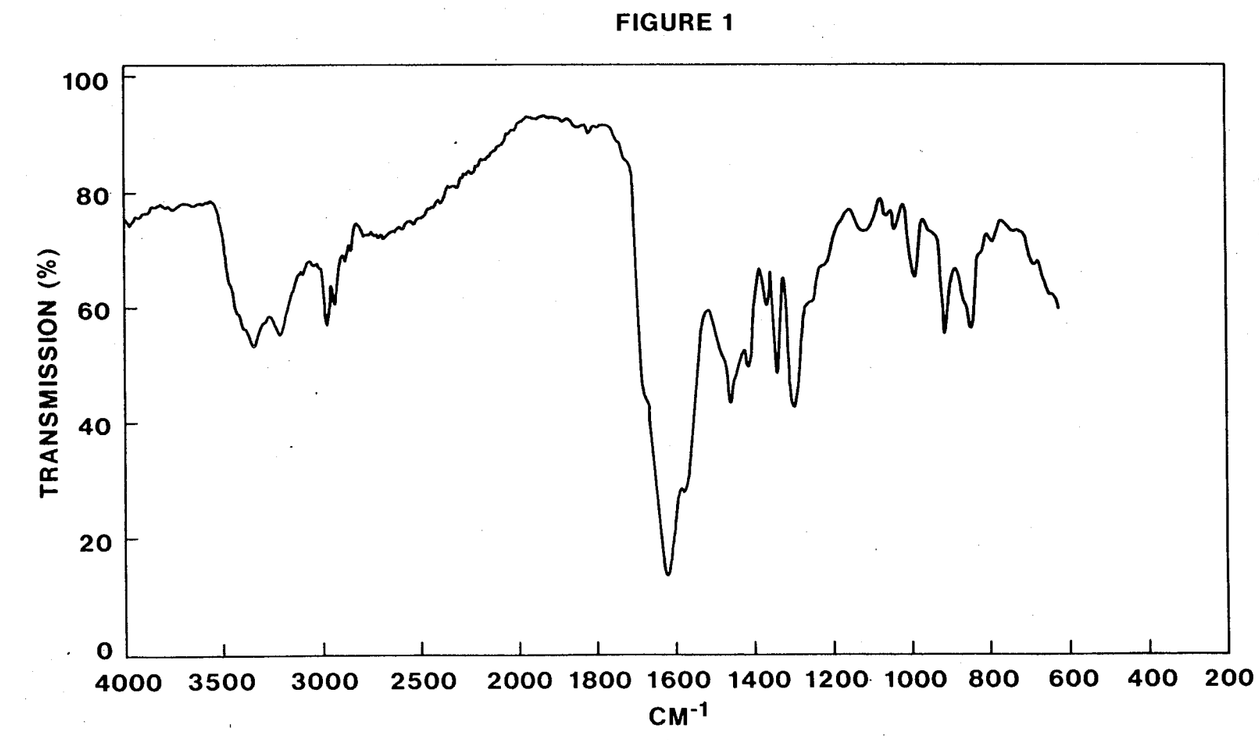
FIG. 1 Infrared absorption spectrum of antibiotic U-68,204.

Infrared Absorption Spectrum: Antibiotic U-68,204 has a characteristic infrared absorption spectrum using the attenuated internal reflectance technique as shown in FIG. 1 of the drawings. Peaks are observed at the following wavelengths.

| Band | |
|---|---|
| Freq.[1] | Inten.[2] |
| 3350 | W |
| 3210 | W |
| 2970 | W |
| 2930 | W |
| 1610 | S |
| 1575 | sh |
| 1460 | W |
| 1410 | W |
| 1365 | W |
| 1340 | W |
| 1300 | M |
| 990 | W |
| 910 | W |
| 845 | W |

[1]Wave numbers (cm$^{-1}$)
[2]S = Strong
M = Medium
W = Weak
sh = shoulder

Figure 2:
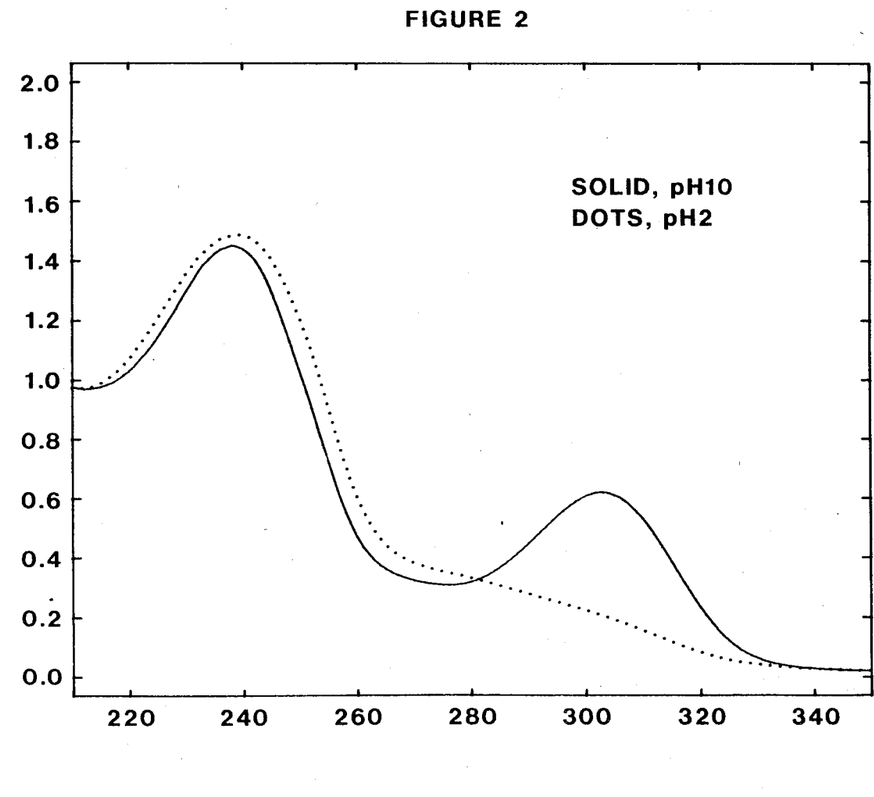
FIG. 2 UV spectrum of U-68,204.

UV Spectrum: The UV spectrum at pH 10 for a 0.0125 mg/ml solution gave maxima at $A_{303}=0.6199$ ($\epsilon=13,200$) and $A_{238}=1.452$ ($\epsilon=31,025$). At pH 2 there was a single maximum with $A_{239}=1.489$ ($\epsilon=31,800$). The UV spectra are shown in FIG. 2.

Figure 3:
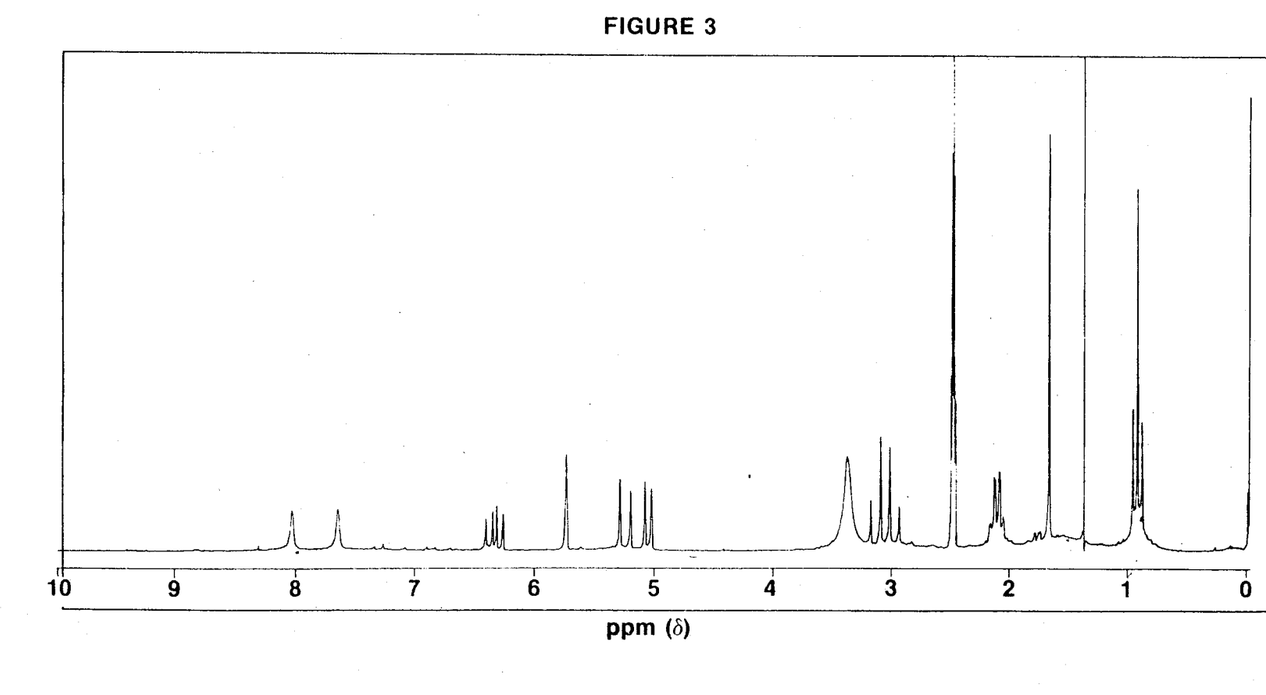
FIG. 3 $^1$H-Nuclear Magnetic Resonance (NMR) spectrum of antibiotic U-68,204.

$^1$H-Nuclear Magnetic Resonance (NMR) Spectrum: The $^1$H-NMR spectrum of antibiotic U-68,204 is shown in FIG. 3 of the drawings. The $^1$H-NMR spectrum was recorded on a Varian CFT-80 Spectrometer in a solution (ca. 0.3 ml., ca 150 mg/ml) of the sample of the antibiotic in deutero chloroform ($CDCl_3$). The spectrum was calibrated against tetramethylsilane and frequencies were recorded in ppm downfield from tetramethylsilane.

Figure 4:
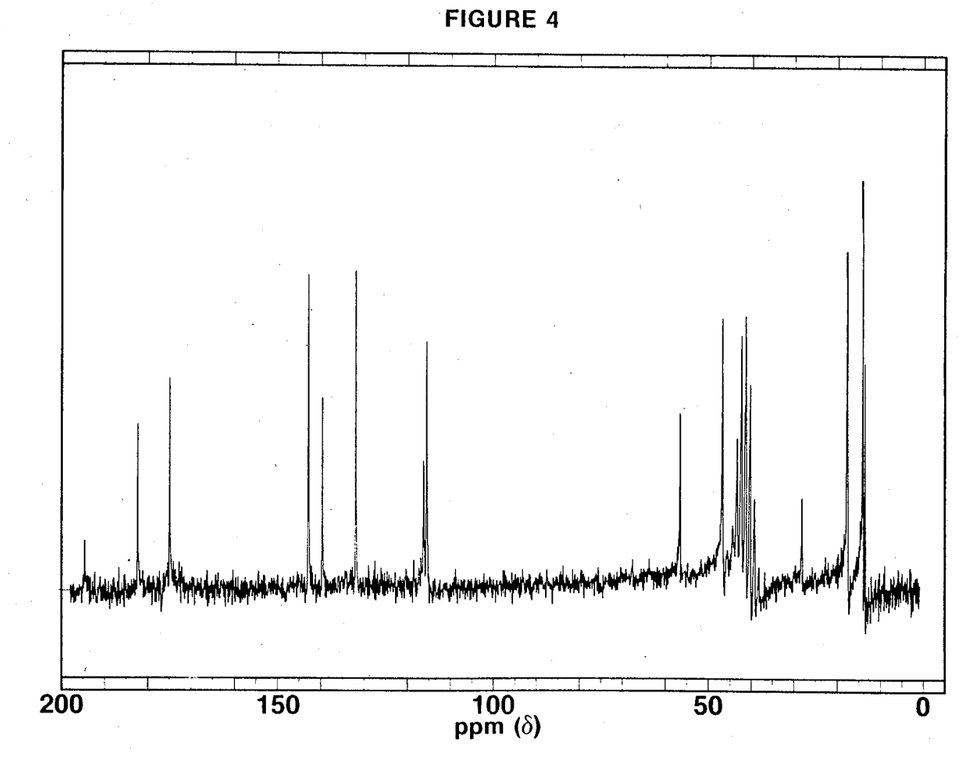
FIG. 4 $^{13}$C-NMR spectrum of U-68,204.

$^{13}$C-NMR Spectrum: The spectra were recorded on a CFT-80 spectrophotometer and are shown in FIG. 4. Crystalline samples of the free acid and of the ammonium salt gave the following results:

| The Acid | The Salt |
|---|---|
| 195δ, S | 196δ, S |
| 182, S | 191, S |
| 175, S | 174, S |
| 143, D | 144, D |
| 140, S | 137, D |
| 132, D | 136, S |
| 116, S | 112, T |
| 115, T | 105, S |
| 56, S | 59, S |
| 47, T | 49, T |
| 17, Q | 18, Q |
| 14, T | 15, T |
| 13, Q | 13, Q |

δ = ppm from internal TMS
S = singlet
D = doublet
T = triplet
Q = quartet

Optical Rotation: $[\alpha]_D^{25} = +177°$ (c=0.8925, ethanol).

Solubilities: Antibiotic U-68,204 is soluble in most organic solvents; it is not soluble in water.

Antimicrobial Spectrum of Antibiotic U-68,204: Antibiotic U-68,204 is active against various Gram-positive bacteria as shown in the follow table.

| MINIMUM INHIBITORY CONCENTRATION | | |
|---|---|---|
| Organism Name | Culture UC# | mcg/ml |
| *Staphylococcus aureus* | 76 | 75 |
| *Staphylococcus aureus* | 6675 | 75 |
| *Staphylococcus aureus* | 3665 | 75 |
| *Staphylococcus aureus* | 6685 | 600 |
| *Streptococcus pyogenes* | 152 | >600 |
| *Streptococcus pneumoniae* | 41 | >600 |
| *Streptococcus faecalis* | 694 | >600 |
| *Escherichia coli* | 311 | 600 |
| *Klebsiella pneumoniae* | 58 | 300 |
| *Enterobacter cloacae* | 9382 | >600 |
| *Pseudomonas aeruginosa* | 6676 | >600 |
| *Pseudomonas aeruginosa* | 6432 | >600 |
| *Pseudomonas aeruginosa* | 6954 | >600 |

| MINIMUM INHIBITORY CONCENTRATION -continued | | |
|---|---|---|
| Organism Name | Culture UC# | mcg/ml |
| *Pseudomonas aeruginosa* | 6955 | 19 |
| *Pseudomonas aeruginosa* | 9027 | 37.5 |
| *Serratia marcescens* | 6888 | >600 |
| *Citrobacter freundii* | 3507 | >600 |
| *Haemophilus influenzae* | 6482 | 9.4 |
| *Haemophilus influenzae* | 6483 | 19 |

The assay is a standard tube dilution assay using BHI (Brain Heart Infusion medium—Difco).

"UC" is a registered trademark of The Upjohn Company Culture Collection.

The structure of Antibiotic U-68,204, along with the assignments of the CMR and PMR chemical shifts, is shown in Chart II.

THE MICROORGANISM

The microorganism used for the production of antibiotic U-68,204 is a biologically pure culture of *Streptomyces thiolactonus* NRRL 15439.

A subculture of this microorganism can be obtained from the permanent collection of the Northern Regional Research Laboratory, U.S. Department of Agriculture, Peoria, Ill., U.S.A. A viable subculture was deposited on May 25, 1983, and its accession number in this depository is NRRL 15439. It should be understood that the availability of the culture does not constitute a license to practice the invention in derogation of patent rights granted with the subject instrument by governmental action.

The microorganism of this invention was studied and characterized by Alma Dietz of The Upjohn Research Laboratories.

*Streptomyces thiolactonus* NRRL 15439

Color characteristics

Aerial mycelium predominantly blue. Melanin-positive. The color pattern on Ektachrome is given in Table 1. Reference color characteristics are given in Table 2. The culture may be placed in the Blue (B) color series of Tresner and Backus [Tresner, H. D., and E. J. Backus. 1963. System of color wheels for streptomycete taxonomy. Appl. Microbiol. 11:335–338].

Microscopic Characteristics

Spores are in chains that appear to be tight spirals when observed with the phase contrast microscope. The chains appear loosely coiled when observed with the scanning electron microscope. The spores are spherical to slightly elliptical and are covered with short spines and fine hairs. The spores measure 0.74×0.65 μm in size.

Growth on Carbon Compounds

The synthetic medium of Shirling & Gottlieb [Shirling, E. B., and D. Gottlieb. 1966] and methods for characterization of Streptomyces species [Int. J. Syst. Bacteriol. 16:313–340] were used for this determination. Growth was good on the positive control (D-glucose), L-arabinose, sucrose, D-xylose, D-mannitol, D-fructose, rhamnose, and raffinose. There was no growth in cellulose. Growth on the negative control ((synthetic medium (ISP-9) without added carbon compound)) was doubtful.

Whole Cell Analysis

L-Diaminopimelic acid was detected in whole-cell hydrolysates.

Culture Characteristics

General characteristics are given in Table 3.

Temperature

Growth on Bennett's, Czapek's sucrose, and maltose-tryptone agars was fair at 18° C., good at 24°–45° C., and poor at 55° C.

*Streptomyces thiolactonus* NRRL 15439 is readily distinguished macroscopically by its blue aerial growth and red-brown-to-brown reverse colors on many media used for characterizing Streptomyces species. Cultures with blue aerial growth have been the subject of a number of publications (the Caeruleus series of Baldacci [Baldacci, E. 1959. Extension of the classification of the actinomycetes. Mikrobiologiya (Trans.) 28:258–267], the Coerulescens series of Gauze [Gauze, G. F., T. P. Preobrazhenskaya, E. S. Kudrina, N. O. Blinov, I. D. Ryabova, and M. A. Iveshnikova. 1957. Problems in the classification of antagonistic actinomycetes. State Publishing House for Medical Literature, Moscow. English edition translated by Fritz Danga; David Gottlieb (ed.). The American Institute of Biological Sciences, Washington, D.C.], the prasinus or azureus-glaucus grouping of Hütter [Hütter, R. 1967. Systematik der Streptomycetes unter besonderer Berücksichtigung der von ihnen gebildeten Antibiotica. S. Karger, Basel], and the viridochromogenes (blue spore) series of Trejo and Bennett [Trejo, W. H. and R. E. Bennett. 1963. Streptomyces species comprising the blue-spore series. J. Bacteriol. 85:676–690]. Grouping of cultures with blue aerial growth is found in Küster [Küster, E. 1972. Simple working key for the classification and identification of named taxa included in the International Streptomyces Project. Int. J. Syst. Bacteriol. 22:139–148] and in Tables 17.45b–e in Family VII. Streptomycetaceae Waksman and Henrici 1943, by Pridham and Tresner in Bergey's Manual, 8th ed. [Pridham, T. G., and H. D. Tresner. 1974. Part 17. Actinomycetes and related organisms. Family VII. Streptomycetaceae Waksman and Henrici 1943. Genus I. Streptomyces Waksman and Henrici 1943. Pages 819–824 in Buchanan and Gibbons, eds., Bergey's Manual of Determinative Bacteriology, 8th ed. The Williams and Wilkins Co., Baltimore]. Most cultures with blue aerial growth are melanin-positive, grow well on carbon compounds in the synthetic medium of Shirling and Gottlieb [Shirling, E. B., and D. Gottlieb. 1966. Methods for characterization of Streptomyces species. Int. J. Syst. Bacteriol. 16:313–340], are thermoduric, and are noted for the production of distinctly different antibiotics. These properties can be determined by reading the descriptions of the blue cultures on pages 819–824 of Bergey's Manual, 8th ed. [Pridham, T. G., and H. D. Tresner. 1974. Part 17. Actinomycetes and related organisms. Family VII. Streptomycetaceae Waksman and Henrici 1943. Genus I. Streptomyces Waksman and Henrici 1943. Pages 819–824 in Buchanan and Gibbons, eds., Bergey's Manual of Determinative Bacteriology, 8th ed. The Williams and Wilkins Co., Baltimore] and the original citations given with the descriptions.

The culture characterized in this report differs from those in the references cited in its macro- and micro-morphology, its general cultural characteristics, and in its production of the new antibiotic U-68,204 (a new thiolactone). It is proposed that this new culture be designated *Streptomyces thiolactonus* Dietz sp. n. It is understood that, in accordance with the Rules of Nomenclature of Bacteria [Lapage, S. P., P. H. A. Sneath, E. F. Lessel, V. B. D. Skerman, H. P. R. Seeliger, and W. A. Clark, ed. 1975. International Code of Nomenclature of Bacteria, 1976 Revision. American Society for Microbiology, Washington, D.C.], this is the type strain and that, should another strain be found, the type strain would also be the type subspecies.

TABLE 1

Color Characteristics* on Ektachrome [Dietz, A. 1954. Ektachrome transparencies as aids in actinomycete classification. Ann. N.Y. Acad. Sci. 60:152–154]

| Agar Medium | | *Streptomyces thiolactonus* NRRL 15439 | |
|---|---|---|---|
| | | Chip | Color |
| Bennett's | S | 185 | pale blue |
| | R | 59 | dark brown |
| Czapek's sucrose | S | 190 | light bluish gray |
| | R | 59 | dark brown |
| Maltose-tryptone | S | 190 | light bluish gray |
| | R | 59 | dark brown |
| Peptone-iron | S | 159 | dark brown |
| | R | 59 | dark brown |
| 0.1% Tyrosine | S | 190 | pale bluish gray |
| | R | 43 | moderate reddish brown |
| Casein starch | S | 190 | pale bluish gray |
| | R | 77 | moderate yellowish brown |

S = surface
R = reverse
*Growth on media in tubes was photographed after seven days incubation at 28 C. Color was determined by comparison with NBS color chips [SP 440. Color: Universal Language and Dictionary of Names. U.S. Government Printing Office, Washington, D.C. 20402]; [SRM 2106. ISCC-NBS Centroid Color Charts. Office of Standard Reference Material, Room B311, Chem. Building, National Bureau of Standards, Washington, D.C. 20234].

TABLE 2

Reference Color Characteristics*

| Agar Medium | | *Streptomyces thiolactonus* NRRL 15439 | |
|---|---|---|---|
| | | Chip | Color |
| Bennett's | S | 190 | light bluish gray |
| | R | 44 | dark reddish brown |
| | P | 57 | light brown |
| Czapek's sucrose | S | 189 | bluish white |
| | R | 77 | strong yellowish brown |
| | P | 84 | strong yellow |
| Maltose-tryptone | S | 190 | light bluish gray |
| | R | 59 | dark brown |
| | P | 57 | light brown |
| Yeast extract-malt extract (ISP-2) | S | 190 | light bluish gray |
| | R | 59 | dark brown |
| | P | 57 | light brown |
| Oatmeal (ISP-3) | S | 190 | light bluish brown |
| | R | 57 | light brown |
| | P | 76 | light yellowish brown (around growth) |
| Inorganic salts starch (ISP-4) | S | 90 | light bluish gray |
| | R | 91 | dark grayish yellow |
| | P | 32 | brownish pink (around growth) |
| Glycerol-asparagine (ISP-5) | S | 190 | light bluish gray |
| | R | 44 | dark reddish brown |
| | P | 58 | moderate reddish brown |

S = surface
R = reverse
P = pigment
*Color determination was made on growth on plates incubated 14 days at 28 C. Color was determined by comparison with NBS color chips.

TABLE 3

| Culture Characteristics - General | | |
|---|---|---|
| Medium Agar | | *Streptomyces thiolactonus* NRRL 15439 |
| Peptone-iron | S | pale blue-white |
| | R | brown |
| | P | brown |
| | O | melanin positive |
| Calcium malate | S | pale blue-white |
| | R | pale yellow |
| | P | none |
| | O | malate not solubilized |
| Glucose-asparagine | S | trace blue-white |
| | R | pink-tan |
| | P | pink-tan |
| Skim milk | S | very slight trace blue-white |
| | R | maroon |
| | P | maroon around growth |
| | O | casein not solubilized |
| Tyrosine | S | very pale blue-white |
| | R | reddish brown |
| | P | reddish brown |
| | O | tyrosine solubilized |
| Xanthine | S | very pale blue-white |
| | R | dull yellow-cream |
| | P | pale yellow |
| | O | xanthine solubilized |
| Nutrient starch | S | pale blue |
| | R | pale olive |
| | P | pale yellow |
| | O | starch solubilized |
| Yeast extract-malt extract | S | pale blue-white |
| | R | red-orange |
| | P | red-orange |
| Peptone-yeast extract-iron (ISP-6) | S | brown |
| | R | brown |
| | P | brown |
| | O | melanin positive |
| Tyrosine (ISP-7) | S | light tan |
| | R | red-brown |
| | P | red-brown |
| | O | melanin positive |
| Gelatin | | |
| Plain | S | brown ring |
| | P | brown 1/5, tan-brown 4/5 |
| | O | trace liquefaction in brown pigment area (one of three) |
| Nutrient | S | brown ring |
| | P | brown 1/5, tan-brown 4/5 |
| | O | trace liquefaction in brown pigment area (one of three) |
| Broth | | |
| Synthetic nitrate | S | pale yellow pellicle and ring |
| | P | yellow-tan diffusing from pellicle |
| | O | nitrate reduction: + in one, − in two trace bottom growth |
| Nutrient nitrate | S | trace blue aerial growth on surface pellicle |
| | P | brown |
| | O | nitrate reduction: − in all red with zinc dust |
| Litmus milk | S | red-tan ring |
| | P | none |
| | O | slight reduction and peptonization at pH 5.86. |

S = surface
R = reverse
P = pigment
O = other characteristics

The compound of the invention process is produced when the elaborating organism is grown in an aqueous nutrient medium under submerged aerobic conditions. It is to be understood, also, that for its preparation surface cultures and bottles can be employed. The organism is grown in a nutrient medium containing a carbon source, for example, an assimilable carbohydrate, and a nitrogen source, for example, an assimilable nitrogen compound or proteinaceous material. Preferred carbon sources include glucose, brown sugar, sucrose, glycerol, starch, cornstarch, lactose, dextrin, molasses, and the like. Preferred nitrogen sources include cornsteep liquor, yeast, autolyzed brewer's yeast with milk solids, soybean meal, cottonseed meal, cornmeal, milk solids, pancreatic digest of casein, fish meal, distillers' dried solids, animal peptone liquors, meat and bone scraps, and the like. Combinations of these carbon and nitrogen sources can be used advantageously.

Production of the compound by the invention process can be effected at any temperature conducive to satisfactory growth of the microorganism, for example, between about 18° and 40° C., and preferably between about 20° and 28° C. Ordinarily, optimum production of the compound is obtained in about 2 to 15 days. The medium normally remains alkaline during the fermentation. The final pH is dependent, in part, on the buffers present, if any, and in part on the initial pH of the culture medium.

When growth is carried out in large vessels and tanks, it is preferable to use the vegetative form, rather than the spore form, of the microorganism for inoculation to avoid a pronounced lag in the production of the compound and the attendant inefficient utilization of the equipment. Accordingly, it is desirable to produce a vegetative inoculum in a nutrient broth culture by inoculating this broth culture with an aliquot from a soil, agar plug stored in liquid $N_2$, or a slant culture. When a young, active vegetative inoculum has thus been secured, it is transferred aseptically to large vessels or tanks. The medium in which the vegetative inoculum is produced can be the same as, or different from, that utilized for the production of the compound, so long as a good growth of the microorganism is obtained.

A variety of procedures can be employed in the isolation and purification of the compound produced by the subject invention from fermentation beers. Isolation can be accomplished by solvent extraction, and adsorption on non-ionic macroporous resins. Chromatography on silica gel can be used to purify crude preparations of the antibiotic.

In a preferred recovery process, the compound produced by the subject process is recovered from the culture medium by separation of the mycelia and undissolved solids by conventional means, such as by filtration or centrifugation, and resin adsorption of the filtered broth. The antibiotic of the subject invention can be recovered from the filtered beer by resin sorption on a resin comprising a non-ionic macroporous copolymer of styrene cross-linked with divinylbenzene. Suitable resins are Amberlite XAD-2 and XAD-4, according to the procedure disclosed in U.S. Pat. No. 3,515,717. (Amberlite resins are available from Rohm and Haas, Philadelphia, PA.). The antibiotic can be eluted from said resins by using acetone:water 1:1 (v/v).

Resins other than XAD-2, and XAD-4 may be substituted. Charcoal can also be used. Extraction with a solvent like 1-butanol also can be used.

The eluting solvent from the resins will vary from resin to resin. A combination of water and acetone (10:90 v/v) can be used.

Purification of the antibiotic from the resin eluate can be done by chromatography of silica gel and subsequent crystallization from methanol.

Base addition salts (e.g. metal salts, for example, sodium, calcium, magnesium and potassium) and other salts, for example, ammonium and triethyl ammonium of antibiotic U-68,204 can be made by use of standard procedures. These salts can be used for the same purposes as the parent antibiotic.

The following examples are illustrative of the process and product of the invention, but are not to be construed as limiting. All percentages are by weight and all solvent mixture proportions are by volume unless otherwise noted.

EXAMPLE 1

A. Fermentation

A biologically pure culture of *Streptomyces thiolactonus* NRRL 15439 is used to inoculate 500-ml Erlenmeyer seed flasks containing 100 ml of sterile medium consisting of the following ingredients:

| Bacto-Tryptone (Difco) | 0.5 |
|---|---|
| Bacto-Yeast Extract (Difco) | 0.3 |
| Deionized $H_2O$ | 100 ml |
| Approx. pH 7.0 (6.8–7.2) | |

Supplement the above with 1% glucose which has been sterilized separately as a 50% solution.

The seed inoculum is grown for three days at 28° C. on a New Brunswick rotary shaker operating at 250 rpm and having a 2½ inch stroke.

Seed inoculum (5% seed), prepared as described above, is used to inoculate 500-ml Erlenmeyer flasks containing 100 l. of the following sterile medium:

|  | g/liter |
|---|---|
| Cerelose | 20 |
| Corn steep liquor | 20 |
| Pharmamedia | 3 |
| $CaCO_3$ | 4 |
| $(NH_4)_2SO_4$ | 3 |
| $ZnSO_4.7H_2O$ | 0.03 |
| Tap water q.s. to 1 liter. | | pH is adjusted to 7.2 with KOH before sterilization. The inoculated fermentation medium is incubated at a temperature of 28° C. for 2–3 days on a New Brunswick rotary shaker as described above.

A typical fermentation has the following titers of antibiotic in the fermentation broth using a paper disc assay:

| Fermentation | | *Ps. aeruginosa* UC 9027 | | *B. fragilis* UC 6513 | |
|---|---|---|---|---|---|
| Days | pH | Inhibition* (mm, diameter) | Biounits | Inhibition* (mm, diameter) | Biounits |
| 2 | 7.5–8.3 | 24–27 | 1.1–2.0 | 23–26 | 1.5–1.8 |
| 3 | 8.0–8.6 | 23–26 | 1.5–2.0 | 23–26 | 1.3–1.8 |

*dipped ¼ in. paper disc

A BU (biounit) is the concentration of the antibiotic which gives a 20 mm zone of inhibition against the test organism.

B. Recovery

Filtered beer at harvest pH (8.5±0.2) is percolated over a bed of XAD-4 (Rohm & Haas Co.) equal in volume to 10% of the beer volume. The resin bed is washed with deionized water until the column elutate is clear. The antibiotic is removed from the column by 1:1 acetone:water (V/V). A gummy solid can be obtained by stripping off the acetone, adjusting the aqueous phase of pH 3 with hydrochloric acid, extracting into methylene chloride (3× with ½ volumes) and stripping off the methylene chloride. At this stage the product is a brown oil.

The filtration can be accomplished using common filter aids such as Dicalite, Harborlite or Celite products. The acetone may be replaced by other volatile, water-miscible solvents such as methanol, ethanol, tetrahydrofuran and acetonitrile. The amount of solvent in the aqueous stream may be varied from 1 to 80% (V/V). The pH adjustment can be made with any convenient organic or mineral acid such as sulfuric, hydrochloric or p-toluenesulfonic. The final pH can range from 0 to 5. The $CH_2Cl_2$ can be replaced with ethyl acetate, 1-butanol, chloroform or like solvents.

A convenient alternative process consists of first extracting the filtered beer (pH 8.5±0.2) with a water-immiscible solvent (such as ethyl acetate, chloroform, methylene chloride, 1-butanol, amyl acetate) to remove lipophilic materials. The aqueous phase can then be adjusted to pH 3 with a mineral acid (such as HCl, $H_2SO_4$, $HClO_4$) and extracted with any of the solvents mentioned above. Antibiotic U-68,204 is isolated as a brown oil after stripping the dried ($MgSO_4$, $Na_2SO_4$) and filtered organic extract.

Other resins may be used such as XAD-2, XAD-7 and XE-348 (all Rohm & Haas), or charcoal. Solvents mentioned above for XAD-2 can be used for elution purposes from these resins.

Advantage may be taken of the acidic nature of Antibiotic U-68,204. The antibiotic can be removed from filtered beer using anion exchange resins such as Dowex 1 (Dow Chem. Co.), IRA 938 (Rohm & Haas), DE52 (Whatman), or DEAE Sephadex (Pharmacia). These resins can be in the chloride, acetate, hydroxide or other convenient form. Elution can be accomplished using solutions of ammonium chloride, ammonium hydroxide, sodium chloride, potassium acetate, pyridinium acetate, or the like. Desalting can be done on one of the neutral resins described above.

C. Purification

The brown oil, obtained above, is subjected to the following purification procedure:

The oil is suspended in 30 ml of 9:1 $MeOH:H_2O$ and the solution is passed over a column of DE52 ($OH^-$) (bed vol. 600 ml). After passing 500 ml of deionized water over the column, a step gradient is started. The gradient consists of sequential elution with 500 ml each of 0.05, 0.1 and 0.3M NaCl solutions. Fractions of 20 ml each are collected throughout. Fractions 36–67 are pooled. The pool amounts to 1.5 L and assays at 8 BU/ml (12,000 BU total).

The pool (1.5 L) is desalted by percolating it over a 500 ml bed of XAD-4. The column is washed with 500 ml of water and eluted with 25% acetone in water (V/V). The active fractions are pooled, concentrated to an aqueous phase, and lyophilized. The brown oil amounts to 550 mg at 15 BU/mg. The value at 303 nm is 10 which indicates this is about 25% pure antibiotic U-68,204. This product is also suitable for final purification by CCCD. This product is now loaded into a 500 tube CCCD machine. The solvent is 6:5:4 chloroform:methanol:pH 4.2 acetate buffer molarity. The K value is 0.7 (tubes 185–220 are pooled).

This pool is acidified with 1N HCl and the phases are separated. The upper phase is extracted twice with half-volumes of chloroform. The combined organic phases are dried with magnesium sulfate, filtered and concentrated on a rotary evaporator at a temperature of 40° C. under aspirator vacuum. The residue is dissolved in 25 ml of methanol and filtered through a 5 micron Gelman syringe filter membrane. The filtrate is concentrated on a rotary evaporator. The oily residue is dissolved in 0.1N $NH_4OH$ and the solution is lyophilized. The yield is 73.5 mg of slightly yellow solid antibiotic U-68,204.

The yellowish solid obtained from CCCD as described above is further treated as follows:

Dissolve 670 mg of the yellow solid in 20 ml of 0.1N $NH_4OH$ and acidify to pH 2 using 1N HCl. Extract the milky white ppt into $CH_2Cl_2$ (3× w. equal volumes). Combine the organic phases. Dry with $MgSO_4$ and filter through a medium porosity sintered glass funnel. The methylene chloride solution is poured into 75 ml of cyclohexane and the methylene chloride is evaporated by placing the flask in a warm-water bath. At the point where cloudiness persists, the flask is removed. Crystallization begins at room temperature and after three hours, the flask is cooled to 5° C. for 10 hrs. The white plates are collected and dried at room temperature in vacuo. A yield of 429 mg of an essentially pure preparation of antibiotic U-68,204 is obtained.

The product can also be purified and crystallized in a number of salt forms. In this case, the crystallization solvents are reversed because of the greatly increased polarity of the salt forms. The volatile solvent should now be polar, such as water or methanol. To this should be added a less polar, miscible solvent such as acetone, acetonitrile or ethyl acetate.

Salts can be made of any metal from Groups 1–8 of the Periodic Chart of the Elements. Examples include calcium, sodium, silver, titanium and tungsten. The two alternative procedures described above can be employed for their synthesis. In addition, salts from amines such as mono-, di- and tri-alkyl amines can be prepared also. These include dimethylamine, dicyclohexylamine, benzylamine, adamantylamine, trioctylamine and cinchonidine.

Salts, acylates and ethers of antibiotic U-68,204 can be used for the same biological purposes as antibiotic U-68,204.

The ammonium salt is prepared by elution of antibiotic U-68,204 from a DE52 column with $NH_4OH$. It also can be prepared by neutralization of solutions containing antibiotic U-68,204 with $NH_4OH$.

The sodium salt can be prepared by eluting antibiotic U-68,204 from a DE52 column with sodium chloride.

The di- and tri-trimethylsilyl (TMS) derivatives can be made for the purpose of GC-MS analysis by heating samples containing antibiotic U-68,204 with bistrimethylsilyltrifluoroacetamide (BSTFA) and chlorotrimethylsilane. The monotrifluoroacetyl derivative can be prepared for GC-MS by using trifluoroacetic anhydride as the acylation reagent.

Numerous variations on trimethylsilyl can be made. These include butyldimethylsilyl, triphenylsilyl and butylethylmethylsilyl. They can be added 1, 2 or 3 units per molecules of U-68,204 to give mono-, di- and tri-silylated derivatives. Acylation can be accomplished using various carboxylic acids such as benzoic, trifluoroacetic, heptafluorobutyric, hexadecanoic or tiglic acids. In addition, ethers can be made such as the methyl, ethyl or benzyl ether of U-68,204. Combination derivatives can be made such as the benzyl ether of the acetate, mono- or di-TMS ethers. These are all standard procedures well known to persons skilled in the art.

CHART I

Thiolactomycin

Thiotetromycin

Citreothiolactone

-continued
CHART I

Antibiotic U-68,204

CHART II

I
CMR Assignments

I
PMR Assignments

We claim:
1. A biologically pure culture of the microorganism *Streptomyces thiolactonus*, having the identifying characteristics of NRRL 15439, said culture being capable of producing the antibiotic U-68,204 in a recoverable quantity upon fermentation in an aqueous nutrient medium containing assimilable sources of carbon, nitrogen and inorganic substances.

* * * * *